(12) United States Patent
Xu

(10) Patent No.: US 7,820,871 B2
(45) Date of Patent: *Oct. 26, 2010

(54) BIOLOGICAL WOUND DRESSING AND METHOD OF MAKING

(75) Inventor: Guo-Feng Xu, Guangzhou (CN)

(73) Assignee: Grandhope Biotech Co., Ltd. (CN)

( * ) Notice: Subject to any disclaimer, the term of this patent is extended or adjusted under 35 U.S.C. 154(b) by 0 days.

This patent is subject to a terminal disclaimer.

(21) Appl. No.: 11/639,690

(22) Filed: Dec. 15, 2006

(65) Prior Publication Data

US 2007/0142763 A1    Jun. 21, 2007

(30) Foreign Application Priority Data

Dec. 20, 2005   (CN)   ................... 2005 1 0120791

(51) Int. Cl.
*A61F 13/00*  (2006.01)
*A61B 19/00*  (2006.01)

(52) U.S. Cl. ............ 602/48; 602/900; 602/901; 128/898

(58) Field of Classification Search ............ 602/48, 602/41, 42; 604/304–308; 424/551, 550, 424/521

See application file for complete search history.

(56) References Cited

U.S. PATENT DOCUMENTS

| | | | |
|---|---|---|---|
| 3,974,526 A | 8/1976 | Dardik et al. | |
| 5,080,670 A | 1/1992 | Imamura et al. | |
| 5,217,492 A | 6/1993 | Guire et al. | |
| 5,290,217 A | 3/1994 | Campos | |
| 5,416,074 A | 5/1995 | Rabaud et al. | |
| 5,447,536 A | 9/1995 | Girardot et al. | |
| 5,549,666 A | 8/1996 | Hata et al. | |
| 5,733,339 A | 3/1998 | Girardot et al. | |
| 5,741,283 A | 4/1998 | Fahy | |
| 5,758,420 A | 6/1998 | Schmidt et al. | |
| 5,955,110 A * | 9/1999 | Patel et al. | 424/551 |
| 6,008,292 A * | 12/1999 | Lee et al. | 525/54.1 |
| 6,090,995 A | 7/2000 | Reich et al. | |
| 6,106,555 A | 8/2000 | Yang | |
| 6,117,979 A | 9/2000 | Hendriks et al. | |
| 6,177,514 B1 | 1/2001 | Pathak et al. | |
| 6,241,981 B1 | 6/2001 | Cobb et al. | |
| 6,251,117 B1 | 6/2001 | Kringel et al. | |
| 6,458,889 B1 | 10/2002 | Trolisas et al. | |
| 6,666,892 B2 * | 12/2003 | Hiles et al. | 623/23.72 |
| 7,053,051 B2 | 5/2006 | Hendriks et al. | |
| 7,060,103 B2 | 6/2006 | Carr, Jr. et al. | |
| 7,077,851 B2 | 7/2006 | Lutze et al. | |
| 2002/0042473 A1 | 4/2002 | Trolisas et al. | |
| 2002/0081564 A1 | 6/2002 | Levy et al. | |
| 2002/0091445 A1 | 7/2002 | Sung et al. | |

(Continued)

FOREIGN PATENT DOCUMENTS

WO    WO 9822158    5/1998

(Continued)

*Primary Examiner*—Patricia M Bianco
*Assistant Examiner*—Tarla R Patel
(74) *Attorney, Agent, or Firm*—Raymond Sun

(57) ABSTRACT

A biological wound dressing is made by a method that includes the steps of providing a natural animal tissue that has a substrate, crosslinking and fixing the substrate, minimizing the antigens from the substrate, and incorporating an active layer in the substrate.

21 Claims, 1 Drawing Sheet

U.S. PATENT DOCUMENTS

| | | |
|---|---|---|
| 2002/0099448 A1* | 7/2002 | Hiles et al. ............... 623/23.61 |
| 2002/0103542 A1 | 8/2002 | Bilbo |
| 2002/0138152 A1 | 9/2002 | Francis et al. |
| 2003/0013989 A1* | 1/2003 | Obermiller et al. .......... 600/567 |
| 2004/0202625 A1 | 10/2004 | Daniloff et al. |
| 2005/0136543 A1 | 6/2005 | Torres et al. |
| 2008/0195229 A1 | 8/2008 | Quijano et al. |

FOREIGN PATENT DOCUMENTS

| | | |
|---|---|---|
| WO | WO 9822158 A2 * | 5/1998 |
| WO | WO 0032250 | 6/2000 |
| WO | WO 0032250 A * | 6/2000 |

* cited by examiner

BIOLOGICAL WOUND DRESSING AND METHOD OF MAKING

BACKGROUND OF THE INVENTION

1. Field of the Invention

The present invention relates to a medical prosthesis for human implantation, and in particular, to a biological wound dressing for protecting a wound surface during wound treatment.

2. Description of the Prior Art

The human body itself is equipped with a perfect repair mechanism for wounds so that many moderate and small wounds can heal themselves by the body's inherent repair system if the wound surface is protected from infections. In general, the treatment of an external wound includes first cleaning and then sterilizing the wound surface, followed by protecting the wound surface with a wound protective dressing to prevent post-infection. Accordingly, a fast development pace has been seen in recent years for protective dressing materials, and various protective wound dressings have been marketed.

However, these protective materials are mostly films of synthetic materials, such as silicone rubber gel film, polyamide film, nylon film, Dacron film, polyethylene film, polypropylene film, etc. These synthetic materials have gradually been found to have poor tissue compatibility and unsatisfactory treatment effect after being used for a certain period of time.

Accordingly, some scientists have attempted to prepare wound dressings using natural biological materials such as collagen, but collagen has poor mechanical strength and requires reinforcement with synthetic film. Such collagen and synthetic material composite films have improved tissue compatibility, but the flexibility is reduced due to increased thickness, and also suffer from poor gas permeability and poor application property.

Some scientists have also utilized chitin and chitin-collagen composite materials to produce protective films, but these films also suffer from poor mechanical strength, poor durability, and poor flexibility, and have not been widely applied.

Pig skin has also been utilized to produce wound dressings in recent years, but the treatment techniques are confined to the traditional glutaraldehyde fixation and chrome tanning method without special treatment for elimination of antigens, thereby exposing the patient to residual toxicity and potential rejection reactions resulting from incomplete elimination of antigens. Such pig skin products also exhibit poor flexibility with enlarged pores after drying so that the bacterial barrier property is poor, and the application property and treatment effect are not ideal, which limits their wide use and application.

Pig small intestine submucosa (SIS) has also been utilized to produce wound dressings, but the treatment used for antigen elimination is a cellular removal technique. However, the protein in the tissue still has remaining antigenicity because antigen determinants exist in many specific sites and their specific conformations. Although the outcome of the acellular SIS based wound dressing is acceptable, there are still improvements that need to be made.

SUMMARY OF THE DISCLOSURE

It is an object of the present invention to provide a biological wound dressing having good biocompatibility, having durable flexibility, that is gas permeable but impenetrable to bacteria, that is convenient to use, and having a simple method of preparation thereof.

In order to accomplish the objects of the present invention, the present invention provides a biological wound dressing which is made by a method that includes the steps of providing a natural animal tissue that has a substrate, crosslinking and fixing the substrate, minimizing the antigens from the substrate, and incorporating an active layer in the substrate.

DETAILED DESCRIPTION OF THE PREFERRED EMBODIMENTS

Figure 1:
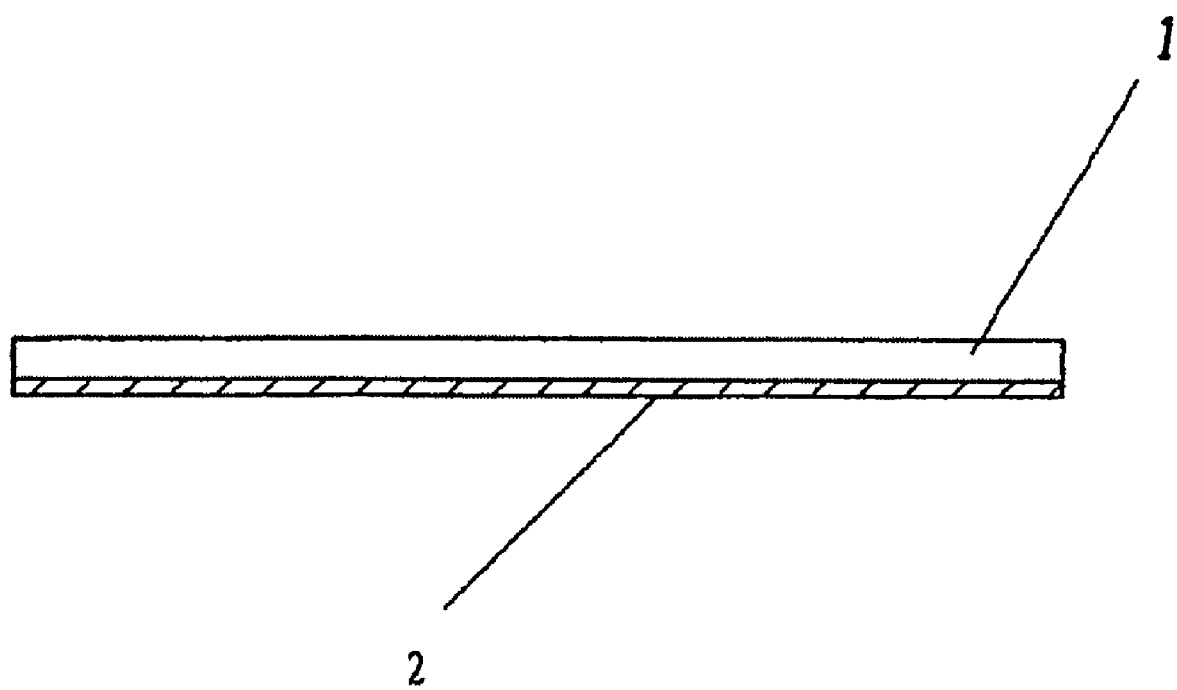
FIG. 1 is a cross-sectional view of a biological protective wound dressing according to one embodiment of the present invention.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The present invention provides a biological wound dressing having a substrate prepared from animal intestinal membrane, treated by crosslinked fixation with a non-aldehyde fixative, and having its antigens minimized.

Animal tissues are easily degraded or decomposed by microorganisms, so that crosslinking and fixation with a fixative is required. Conventionally, glutaraldehyde is utilized as a fixative, but glutaraldehyde produces toxic radicals. Aldehydes undergo crosslinking with proteins through the acetal reaction and toxic aldehydes are released when the crosslinked products are degraded, so that products fixed with an aldehyde have long-term residual toxicity. When non-aldehyde fixatives such as epoxides, diacyl diamides, diisocyanates, polyethylene glycol or carbodiimides are utilized as fixatives in place of aldehydes, this toxicity problem can be minimized or even eliminated. For example, when an epoxide is utilized to replace aldehyde-type fixatives, a ring-opening/crosslinking reaction occurs readily because epoxides are unstable, but the crosslinking product can be made very stable and not easily degraded by controlling the reaction condition. It is slowly degraded into polypeptides and amino acids and absorbed only when tissue growth and regeneration begin to devour it by secreting kallikrein, fibrinolysin and glucocorticoid hormone to help collagenase in the degradation. Such kind of passive degradation and tissue regeneration are occurring simultaneously which is beneficial to tissue regenerative repair while having no residual toxicity of aldehydes. According to modern immunological theory, the antigenicity of animal tissues stems mainly from active groups located at specific sites and in specific conformations, and these active groups include —OH, —NH2, —SH, etc. The specific conformations result mainly from some specific hydrogen bonding formed by spiral protein chains. The specific sites and conformations are called antigen determinants. One or more active reagents (e.g., acid anhydrides, acyl chlorides, amides, epoxides, etc.) that react readily with these groups are utilized to bond with and block these groups when treating animal tissues so that the antigens can be effectively minimized or eliminated. Simultaneously, reagents with strong hydrogen bonding (e.g., guanidine compounds) are utilized to replace the hydrogen bonding that gives the specific configurations so that the configurations are altered and the antigenicity is effectively eliminated.

Method

A method of preparing the biological wound dressing according to the present invention comprises the following steps, and uses animal tissue as the substrate:

1. Selection of materials: Fresh animal small intestines are collected. One example is animal submucosa.

2. Pretreatment: The small intestines are cleaned and sterilized, and the mucous membrane and lower connective tissues are removed to retain the strong membrane, which is trimmed and dried to provide the substrate.

3. Defatting: Fats and fat-soluble impurities in the substrate are extracted with an organic solvent.

4. Crosslinking fixation: The collagen molecules in the substrate are crosslinked and fixed with a non-aldehyde fixative, as described in greater detail hereinbelow.

5. Minimizing antigens: An active reagent is utilized to block the specific active groups such as —OH, —NH2, —SH, etc., in the proteins of the substrate, and a reagent with strong hydrogen bonding power is utilized to replace the specific hydrogen bonding in the spiral chains of the protein molecules in the substrate and alter its specific configuration.

6. Coupling of active layer: A modified active layer is incorporated on the substrate surface. According to one embodiment, the modified active layer can contain fibronectin, mucin or vitrein that are adhered to the substrate surface by an absorbing/adhering means for forming the modified active layer. According to another embodiment, the modified active layer can be coated with a mixed composition comprising a biological adhesive and a broad-spectrum antibacterial agent to give a controlled-release antibacterial layer.

Fixative

The fixative applied in step 4 of the above method can be a reagent that crosslinks easily with protein molecules and is one or two reagents selected from epoxides, diacyl diamides, diisocyanates, polyethylene glycol or carbodiimides. This fixative may be an epoxy compound that has a hydrocarbon backbone, that is water-soluble, and which does not contain an ether or ester linkage in its backbone. This fixative is described in U.S. Pat. No. 6,106,555, whose entire disclosure is incorporated by this reference as though set forth fully herein. Examples include an epoxide, a diamide, a diisocyanate, a polyethylene glycol, or a carbodiimide, in that the epoxide may be a monocyclic epoxide, or a bicyclic epoxide, or it may be a low poly(epoxide) (such as low poly(ethylene oxide), poly(propylene oxide) or a glycidyl ether). The epoxide may be a monocyclic epoxide

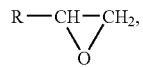

or a dicyclic epoxide

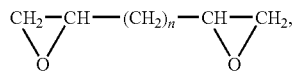

where R=H, $C_nH_{2n+1}$—, n=0-10, and may also be a lower polyepoxide such as polypropylene oxide.

Active Reagents

The active reagents in step 5 of the above method may be low molecular weight organic acid anhydrides, acyl chlorides, acylamides or monocyclic oxides, and the reagents having strong hydrogen bonding power are guanidine compounds.

Active Layer

In one embodiment, the modified active layer in step 6 of the above method may contain fibronectin or mucin or vitrein which are capable of adhering to cells and increasing the adhesion of the wound protective film to epithelial cells and fibroblasts so that epithelial cells and fibroblasts are accumulated to promote wound repair and healing. In another embodiment, the modified active layer in step 6 can be furnished with a controlled-release film containing a broad-spectrum antibacterial agent so that the wound dressing can demonstrate antibacterial and anti-infectious effects.

The present invention provides the following advantages. The biological wound dressing of the present invention is prepared from thin and tough animal intestinal membrane so that it is lightweight, soft and easy to use. Intestinal membrane is a semi-transparent membrane with small and dense micropores and is gas permeable with good permeability while being impenetrable to bacteria, and because it has been treated by multimode minimization of the antigens, the immunogenicity is effectively eliminated. Additionally, the surface is actively modified to facilitate accumulation of epithelial cells and fibroblasts so that wound healing can be promoted. Or a slow-release antibacterial agent is furnished to enhance anti-infection activity so that the application property and wound protective effect are superior compared with those of the dressing materials or protective film prepared from pig skin.

Example 1

As shown in FIG. 1, the biological wound dressing comprises a substrate 1 prepared from animal intestinal membrane by crosslinking and fixing with a non-aldehyde fixative and by minimizing antigens, in that a modified active layer 2 containing fibronectin, mucin or vitrein capable of adhering cells or slow-release antibacterial layer 2 is incorporated on the surface of substrate 1.

The method of preparation of the biological wound dressing of the present invention includes the following steps:

1. Selection of materials: Fresh animal small intestines (such as submucosa) are collected.

2. Pretreatment: The small intestines are cleaned and sterilized and the mucous membrane and lower connective tissues are removed to retain the strong membrane, which is trimmed and dried to provide the substrate 1.

3. Defatting: Fats and fat-soluble impurities in the substrate 1 are extracted with an organic solvent.

4. Crosslinking fixation: The collagen molecules in the substrate 1 are crosslinked and fixed with an epoxide at room temperature.

5. Minimizing antigens: The specific active group, namely —OH or —NH$_2$ or —SH, in the proteins of the substrate is blocked with active reagent butyric anhydride and the specific hydrogen bonding in the spiral chains of the proteins in the substrate 1 is replaced by using guanidine hydrochloride Tris solution, to alter the configuration.

6. Active modification of the surface: Fibronectin, mucin or vitrein is adhered to substrate surface 1 by an adsorbing/adhering means for forming the modified active layer 2. Alternatively, the surface of the substrate 1 is coated with a mixed composition comprising a biological adhesive and a broad-spectrum antibacterial agent to provide a controlled-release antibacterial layer 2.

7. Post-treatment: The final product is obtained after vacuum drying, shape fixing, packaging and sterilization with epoxides or irradiation.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A method for preparing a biological wound dressing, comprising:
   providing a substrate that is made from natural animal tissue;
   crosslinking and fixing the substrate with non-aldehyde fixatives;
   blocking residual specific active groups in protein molecules of the substrate after fixation by applying at least one active reagent;
   altering the specific conformation of protein molecules of the substrate by a reagent with strong hydrogen bonding power; and
   coupling an active layer to the substrate that includes either a polypeptide or a glucosaminoglycan that has the ability to adhere growth factors after implantation.

2. The method of claim 1, wherein the natural animal tissue is an animal small intestine.

3. The method of claim 2, wherein the natural animal tissue is the submucosa of an animal small intestine.

4. The method of claim 1, wherein the at least one active reagent to block specific active groups in the protein molecules of the substrate can be acid anhydrides, acid chlorides, or acylamides.

5. The method of claim 1, wherein the reagent with strong hydrogen bonding power is a guanidine compound.

6. The method of claim 1, wherein the crosslinking and fixing step includes applying an epoxy compound, a diamide, a diisocyanate, or a carbodiimide.

7. The method of claim 6, wherein the epoxy compound that has a hydrocarbon backbone, that is water-soluble, and which does not contain an ether or ester linkage in its backbone.

8. A biological wound dressing, comprising:
   a substrate that is made from natural animal tissue, the substrate having: (i) been fixed with crosslinking reagents, (ii) residual specific active groups in protein molecules of the substrate that have been blocked by at least one active reagent after fixation by the crosslinking reagents, (iii) specific conformation of protein molecules of the substrate altered by a reagent with strong hydrogen bonding power, and (iv) an active layer coupled thereto, the active layer including either a polypeptide or a glucosaminoglycan that has the ability to adhere growth factors after implantation.

9. The dressing of claim 8, wherein the natural animal tissue is an animal small intestine.

10. The dressing of claim 9, wherein the natural animal tissue is the submucosa of an animal small intestine.

11. The dressing of claim 8, wherein the at least one active reagent to block specific active groups in the protein molecules of the substrate can be acid anhydrides, acid chlorides, or acylamides.

12. The dressing of claim 8, wherein the reagent with strong hydrogen bonding power is a guanidine compound.

13. The dressing of claim 8, wherein the substrate is fixed by an epoxide compound, a diamide, a diisocyanate, or a carbodiimide.

14. The dressing of claim 13, wherein the epoxy compound that has a hydrocarbon backbone, that is water-soluble, and which does not contain an ether or ester linkage in its backbone.

15. A biological wound dressing made by a method comprising:
   providing a substrate that is made from a natural animal tissue;
   crosslinking and fixing the substrate with a non-aldehyde fixative;
   blocking residual specific active groups in protein molecules of the substrate after fixation by applying at least one active reagent;
   altering the specific conformation of protein molecules of the substrate by a reagent with strong hydrogen bonding power; and
   coupling an active layer to the substrate that includes either a polypeptide or a glucosaminoglycan that has the ability to adhere growth factors after implantation.

16. The dressing of claim 15, wherein the natural animal tissue is an animal small intestine.

17. The dressing of claim 16, wherein the natural animal tissue is the submucosa of an animal small intestine.

18. The dressing of claim 15, wherein the at least one active reagent to block specific active groups in the protein molecules of the substrate can be acid anhydrides, acid chlorides, or acylamides.

19. The dressing of claim 15, wherein the reagent with strong hydrogen bonding power is a guanidine compound.

20. The dressing of claim 15, wherein the substrate is fixed by an epoxide compound, a diamide, a diisocyanate, or a carbodiimide.

21. The dressing of claim 20, wherein the epoxy compound that has a hydrocarbon backbone, that is water-soluble, and which does not contain an ether or ester linkage in its backbone.

* * * * *

Disclaimer

7,820,871 B2—Guo-Feng Xu, Guangzhou (CH). BIOLOGICAL WOUND DRESSING AND METHOD OF MAKING. Patent dated October 26, 2010. Disclaimer filed May 18, 2010, by the assignee, Grandhope Biotech Co., Ltd.

The term of this patent shall not extend beyond the expiration date of patent no. 7,820,871.

*(Official Gazette January 10, 2012)*

Disclaimer 7,820,871 B2—Guo-Feng Xu, Guangzhou (CN). BIOLOGICAL WOUND DRESSING AND METHOD OF MAKING. Patent dated October 26, 2010. Disclaimer filed April 11, 2011, by the assignee, Grandhope Biotech Co., Ltd.

The term of this patent shall not extend beyond the expiration date of Patent No. 7,674,289.

*(Official Gazette, February 14, 2012)*